United States Patent [19]

Grimminger et al.

[11] Patent Number: 4,934,201
[45] Date of Patent: Jun. 19, 1990

[54] METHOD AND APPARATUS FOR SUPPLYING SAMPLES FROM A MELT TO A RHEOMETER

[75] Inventors: Albert Grimminger, Leonberg; Heinz Herrmann, Stuttgart; Franz J. Müller, Bietigheim-Bissingen; Hans-Jurgen Nettelnbreker, Ludwigsburg; Bernhard Stöhrer, Pleidelsheim, all of Fed. Rep. of Germany

[73] Assignee: Werner & Pfleiderer GmbH, Stuttgart, Fed. Rep. of Germany

[21] Appl. No.: 272,510

[22] Filed: Nov. 16, 1988

[30] Foreign Application Priority Data

Dec. 5, 1987 [DE] Fed. Rep. of Germany ....... 3741230

[51] Int. Cl.⁵ .............................................. G01N 1/00
[52] U.S. Cl. .............................. 73/864.81; 73/863.11; 73/863.54
[58] Field of Search ........... 73/863.11, 863.44, 863.45, 73/863.51–863.58, 863.81, 863.82, 864.21, 864.81

[56] References Cited

U.S. PATENT DOCUMENTS

| | | | |
|---|---|---|---|
| 2,641,934 | 6/1953 | Werts | 73/863.82 |
| 2,780,094 | 2/1957 | Fink | 73/866.5 |
| 3,138,950 | 6/1964 | Welty et al. | 73/863.56 |
| 3,276,264 | 10/1966 | Banks | 73/863.54 |
| 3,595,087 | 7/1971 | Starks | 73/863.56 |
| 3,831,452 | 8/1974 | Pittenger | 73/863.82 |
| 3,885,437 | 5/1975 | Reagan | 73/863.82 |
| 4,433,587 | 2/1984 | Risdal | 73/863.54 |
| 4,479,393 | 10/1984 | Shores | 73/863.82 |

Primary Examiner—Robert Raevis
Attorney, Agent, or Firm—Ladas & Parry

[57] ABSTRACT

A method and apparatus for removing samples from a plastic melt for measuring the rheological properties of the plastic melt in which melt samples are removed from melt in a melt channel through a hollow probe arranged transversely of the direction of flow of the melt, the probe having an opening for the inlet of the melt samples. The probe is elongated and is displaceable along its axis in a direction transverse of the melt channel while being rotatable around its axis so that the inlet in the probe can be placed in various positions in the melt cross section. The opening of the probe is disposed at the periphery of a circle lying in a radial plane around the longitudinal axis whereby samples can be obtained in a three-dimensionally extending region.

15 Claims, 2 Drawing Sheets

METHOD AND APPARATUS FOR SUPPLYING SAMPLES FROM A MELT TO A RHEOMETER

FIELD OF THE INVENTION

The present invention relates to a method and apparatus for removing a sample of molten plastic from a melt channel in order to measure the rheological properties of the plastic in a rheometer.

DESCRIPTION OF PRIOR ART

The determination of the melt index of plastic materials is effected, as known, in rheometers in which the molten plastic material is fed continuously under the pressure of the melt from the melt channel of a production unit. The melt index is measured batchwise or continuously in capillaries in the rheometer, the time required for the passage or pressure drop of the plastic melt within the capillary region serving as a measure of the viscosity of the melt. Such rheometers are known, for instance, from DE-OS 1,698,291 and DE-OS 1,801,407.

In order to increase product quality and avoid unnecessary rejects, it is necessary for the results of the measurement not only to be accurate but also to be representative of the entire molten stream. Since the properties of the melt vary condiserably in temperature and viscosity locally over the cross section of the molten stream, it is not possible to satisfy this requirement by the known devices. In addition, fundamentally, only relatively small quantities of specimen can be measured in the rheometer within a given time unit.

Thus, in apparatus disclosed in DE-OS 1,698,291, a sample stream is diverted in a stationary probe from an edge layer of the melt channel, which layer is not representative of the entire melt. Flow streams from adjacent regions of the channel cross section are not included in the sample.

SUMMARY OF THE INVENTION

An object of the invention is to provide apparatus which permits removal of a sample from a plastic melt which is representative of the entire cross section of a melt channel.

In accordance with the above and further objects of the invention, there is provided apparatus for supplying samples from a melt to a rheometer which comprises a housing having a melt channel for flow of melt therein, a probe in said melt channel having an inlet for receiving a sample of the melt flowing in the channel and for conveying the sample towards a rheometer and means supporting said probe for displacement in said housing transversely of said melt channel and for rotation in said housing.

By longitudinal displacement of the probe, its inlet opening for melt can travel within the melt channel for sampling different portions of the melt flow and not be limited to removal of a sample at a single location.

Due to the rotatability of the probe, the region for sampling is expanded so that the melt sample can be removed over a wide cross sectional region of the melt channel. Consequently, a representative sample of melt at different points in the melt channel can be obtained.

By providing sleeves for guiding the probe, in accordance with one embodiment according to the invention, the escape of plastic melt along the probe is effectively prevented.

According to a further feature of the invention, the probe is axially displaceable by a threaded drive means which has the advantage that the position of the inlet opening of the probe within the melt channel can be determined on the basis of a visible parameter, namely the length of thread of the probe which protrudes from the housing. The angular position of the inlet opening of the probe with respect to the longitudinal axis of the melt channel can be made visible by providing a marking indicia on the protruding part of the probe.

In order to permit displacement of the probe along the longitudinal axis even with a fixed angular position of the inlet opening of the probe, one of the sleeves is constructed in accordance with another feature of the invention with a turnable and lockable nut.

According to a further embodiment of the invention, the probe, regardless of the guidance of the melt, remains limited to the dimension determined substantially by the cross section of the channel probe so that the handling of the probe is facilitated.

In order to maintain the temperature of the melt constant over the length of travel of the melt sample to the rheometer, it is advantageous, in accordance with a further feature of the invention, to compensate for heat losses by supplying heat to the sample as it flows to the rheometer.

According to a simple and effective construction of the probe, it includes a cylindrical socket extending at right angles to the body of the probe, the socket being provided with the inlet for the melt samples and connecting the inlet to the channel in the probe body.

A further object of the invention is to provide a method by which samples of the melt can be conveyed to a rheometer by transversely displacing the probe in the melt channel and angularly about the axis of displacememt to vary the position of the inlet of the probe in the melt channel to enable different portions of the melt to be introduced into the inlet of the probe.

DETAILED DESCRIPTION OF A PREFERRED EMBODIMENT

Figure 1:
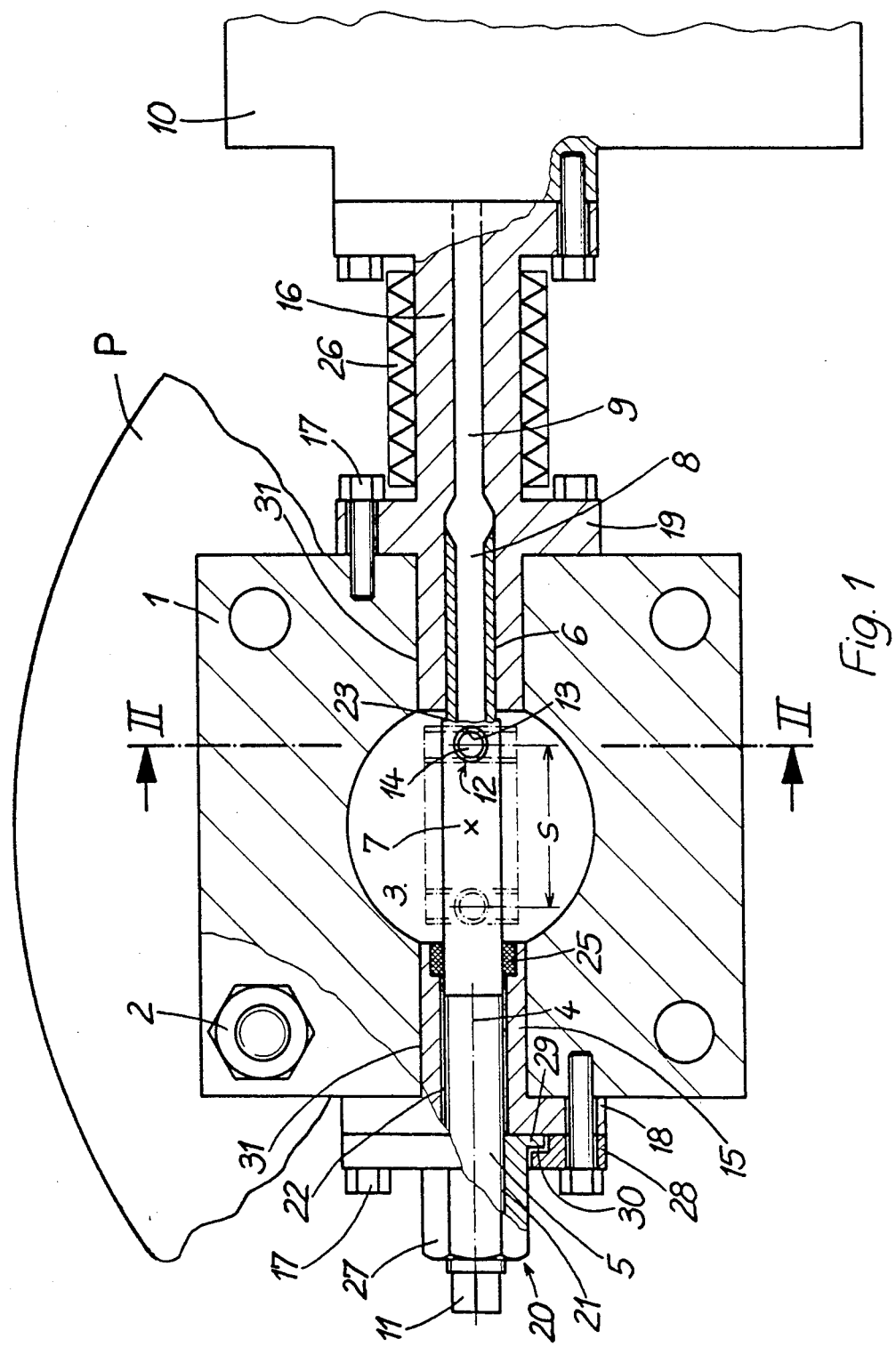
FIG. 1 is a longitudinal sectional view through apparatus according to the invention for removing samples of plastic melt.
Figure 2:
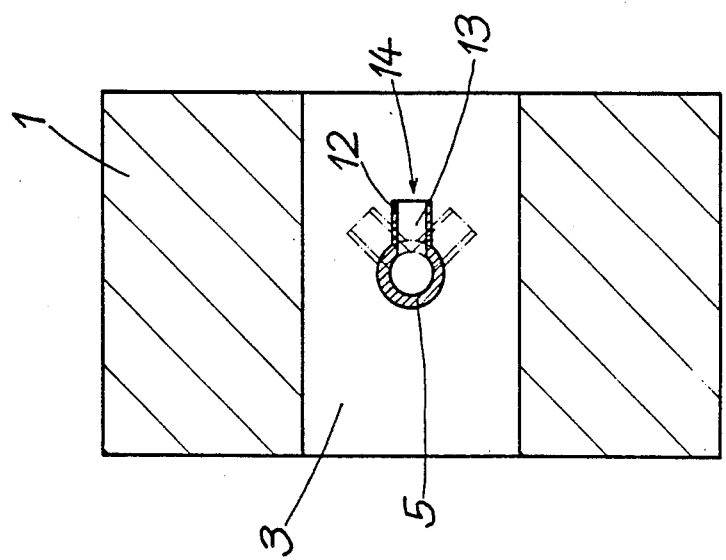
FIG. 2 is a cross section taken along line II—II in FIG. 1.
Figure 3:
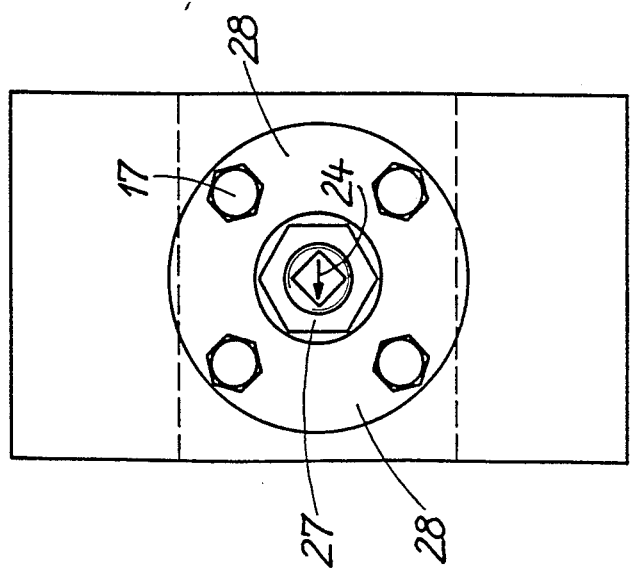
FIG. 3 is an end view of a portion of the apparatus seen from the left in FIG. 1.

Referring to the drawing, therein is shown apparatus according to the invention for removing a sample of molten plastic from a melt flowing from a production unit p such as a melt extruder or the like. In particular, the apparatus of the invention comprises a housing 1 attached by bolts 2 to the production unit which produces plastic material in such a manner that a melt channel 3 in housing 1 is in communication with a discharge region of the production unit p to convey the melt from the unit through the melt channel 3.

A cylindrical probe 5 extends transversely of the melt channel 3 in a bore 6 whose longitudinal axis 4 intersects a central axis 7 of the melt channel 3. The bore 6 is of smaller diameter than the channel 3 and corresponds to the outside diameter of the probe 5. At its left end in FIG. 1, a portion of the cylindrical probe 5 extends out of the housing 1 in order to enable the probe to be moved in a manner to explained later, and for this purpose a square shank 11 is formed at the left end of the probe 5.

At its opposite end, the probe 5 is provided with a bore 8 forming a probe channel extending over a portion of the length of the probe. A connecting socket 12 is integral with probe 5 and has an inlet opening 14 so that melt flowing in channel 3 can be diverted as a melt sample from the melt channel 3 to the probe channel 8. The probe channel 8 is in communication with a passage channel 9 which leads to a rheometer 10. The rheometer 10 is of conventional type and its construction is known to those skilled in the art and requires no detailed discussion herein.

The connection of the probe channel 8 to the melt channel 3 is effected by the connecting socket 12 whose bore 13 opens into the probe channel 8. The inlet opening 14 in the socket admits melt into bore 13 and the melt then flows into the probe channel 8. The connecting socket 12 preferably extends perpendicularly to the longitudinal axis 4 of the probe channel 8. The cross section of the opening 14, and thus essentially also of the bore 13 of the connecting socket 12, is equal to or less than the cross section of the probe channel 8. In this way, clogging of the probe channel 8 is effectively prevented in the case of impurities in the melt. The cross section of the probe channel 8 corresponds to the cross section of the passage channel 9.

For guiding of the probe in the course of its movement, there are sleeves 15 and 16 which are tightly fitted in a bore 31 in housing 1 on both sides of the melt channel 3, the passage channel 9 extending in the longitudinal axial direction through the sleeve 16. The two sleeves 15 and 16 are secured by bolts 17 respectively connecting flanges 18 and 19 on sleeves 15 and 16 to the housing 1. Mounted coaxially with respect to the passage channel 9 is a heating unit 26 on the outer wall of the sleeve 16 for supplying heat to the melt sample to compensate for heat losses which occur in the conducting of the melt sample to the rheometer.

The sleeve 15 is provided with a head assembly 23 comprising a threaded guide 21 which threadably receives a threaded portion 22 of the probe 5.

The guide 21 is formed with a hexagonal nut portion 27 mounted rotatably at the end of the sleeve 15 by means of a flange ring 285. The rotatable mounting of the hexagonal nut 27 is effected by an annular collar 29 rotatably received in a recess 30 in the flange ring 28. The flange ring 28 is fastened, together with the sleeve 15, to the housing 1 by means of the bolts 17.

By placing a wrench on shank 11, the probe 5 can be rotated within the bore 6. In this way, the inlet opening 14 of the connecting socket 12 can be pivoted, as desired, within the melt channel 3.

By holding the square shank 11 and turning the hexagonal nut 27 by means of a box wrench, the attitude of the inlet opening 14 can be held fixed while the probe is longitudinally moved so that the inlet opening 14 can travel longitudinally along a stroke path s. In this way, displacement of the probe 5 is possible even with a fixed adjustment of the angular position of the inlet opening 14 of the probe 5. During operating conditions, turning of the probe 5 is prevented by a sealing and clamping ring 25. An end stop 23, formed by a shoulder at a change in diameter in the probe 5, limits the stroke of the probe to the right in FIG. 1. The probe 5 is limited in its stroke to the left in FIG. 1 by the length of the threaded portion 22 on probe 5. The length of the threaded portion 22 protruding beyond the head assembly 20 represents the position of the inlet opening 14 in its path s within the melt channel 3. In order to indicate the angle of rotation of the inlet opening 14 with respect to the direction of flow of the melt, a directional arrow 24 is provided on the end of the square shank 11, the arrow corresponding to the radial position of the connecting socket 12, and thus of inlet opening 14, with respect to the axis of the probe 5.

In operation, the longitudinal position of the probe along its length of stroke s is fixed and the angle of rotation of the connecting socket 12 with respect to the central axis 7 of the melt channel 3 is then adjusted by hand within a range of between 0° and 30° so that a favorable flow into the inlet opening 14 is obtained.

The region of the removal of the sample from the melt channel 3 thus defines a rectangular cross sectional region within the melt channel 3 the dimensions of which are established, on the one hand, by the length of the connecting socket 12 and its angle of rotation upon the taking of the sample, and, on the other hand, by the displacement length (stroke s) of the probe 5 within the melt channel 3. In this way, the removal of a representative stream of sample is possible at defined positions of the cross section of the melt channel.

By individual sample removal it is thus possible, depending on the type of melt, to remove plastic melt at variable places within the melt channel 3 and to feed the melt to the rheometer 10, so that measurement results which are representative of the entire stream of the melt are obtained.

Although the invention has been described in relation to a specific embodiment thereof, it will become apparent to those skilled in the art that numerous modifications and variations can be made within the scope and spirit of the invention as defined in the attached claims.

What is claimed is:

1. Apparatus for supplying samples from a melt to rheometer comprising a housing having a melt channel, means for connecting the housing to a production unit such that melt produced from the production unit flows through said melt channel, a probe in said housing extending transversely through said melt channel and having opposite ends projecting beyond the melt channel, said probe having inlet means at an intermediate position along its length for receiving a sample of the melt flowing in the melt channel, said probe having a channel communicating with said inlet means and extending at one of the projecting ends of the probe for conveying the sample towards a rheometer, means supporting said probe for displacement in said housing along a longitudinal axis of the probe transversely of said melt channel and for turning of the probe around said longitudinal axis to adjust the position of said inlet means in the melt channel whereby a large cross sectional region of the melt flowing in the melt channel can be sampled and means cooperating with the other of the projecting ends of the probe to enable the probe to be longitudinally displaced and turned.

2. Apparatus as claimed in claim 1 wherein said inlet means has an opening disposed on the periphery of a circle whose center is located on the longitudinal axis of the probe.

3. Apparatus as claimed in claim 2 wherein said means which supports the probe comprises first and second spaced sleeves secured in said housing and respectively rotatably receiving the projecting ends of said probe.

4. Apparatus as claimed in claim 3 wherein said means which enables the probe to be longitudinally displaced and turned comprises a head assembly on said housing including a rotatable but axially fixed threaded guide member, said probe including a threaded portion threadably engaged in said guide member.

5. Apparatus as claimed in claim 4 wherein said means which enables the probe to be longitudinally displaced and turned further comprises a portion of said probe extending from said housing including means by which said probe can be rotated from outside said housing.

6. Apparatus as claimed in claim 4 wherein said threaded guide member is accessible from outside said housing.

7. Apparatus as claimed in claim 3 wherein one of said sleeves has a bore for receiving samples of melt from the probe channel for conveying the samples to the rheometer, said probe channel having a cross section which is equal to or greater than the cross section of said inlet means.

8. Apparatus as claimed in claim 7 further comprising heating means associated with said one of said sleeves for heating the samples of melt therein.

9. Apparatus as claimed in claim 1 wherein said inlet means includes a socket extending perpendicularly of said probe, said socket having an opening for samples of melt.

10. Apparatus as claimed in claim 9 wherein said probe extends perpendicularly to said melt channel.

11. Apparatus as claimed in claim 1 wherein the means which connects the housing to the production unit comprises detachable fastening means enabling the housing and probe to be detachably connected to the production unit so that the melt channel can selectively be brought into communication with a discharge region of the unit.

12. Apparatus as claimed in claim 1 wherein said probe at each of said ends projects beyond the housing.

13. A method of supplying samples from a melt from a production unit to a rheometer comprising attaching a housing to a melt production unit so that melt flows from the production unit through a melt channel in the housing, conveying samples of the melt to a rheometer through an inlet in a probe supported in the housing in the melt channel, displacing the probe along a longitudinal axis thereof transversely of the melt channel and angularly about the longitudinal axis to vary the position of the inlet of the probe in the melt channel to enable different portions of the melt to be introduced into the inlet of the probe, said probe conveying the samples of the melt to the rheometer at one lateral said of the housing whereas the longitudinal and angular displacement of the probe is effected from the other lateral side of the housing.

14. A method as claimed in claim 13 wherein the sample of melt is conveyed through a socket of the probe in a direction perpendicular to the axis of displacement of the probe until the sample reaches a channel in the probe whereafter the sample flows in said channel towards the rheometer.

15. A method as claimed in claim 14 comprising heating the sample as it flows to the rheometer from the probe channel.

* * * * *